United States Patent [19]

Wurtman et al.

[11] Patent Number: 5,118,670

[45] Date of Patent: Jun. 2, 1992

[54] PROCESS AND COMPOSITION FOR INCREASING BRAIN DOPAMINE RELEASE

[75] Inventors: Richard J. Wurtman, Boston; Ian Acworth, Brookline, both of Mass.; Michael Kreutz, Oberhauser; Hendrik Lehnert, Mainz, both of Fed. Rep. of Germany

[73] Assignee: Massachusetts Institute of Technology, Cambridge, Mass.

[21] Appl. No.: 284,074

[22] Filed: Dec. 14, 1988

[51] Int. Cl.$^5$ .................. A61K 37/24; A61K 31/195
[52] U.S. Cl. ...................................... 514/18; 514/21; 514/567
[58] Field of Search .................. 514/18, 567, 21

[56] References Cited

U.S. PATENT DOCUMENTS

| | | | |
|---|---|---|---|
| 3,737,549 | 6/1973 | Plotnikoff | 514/21 |
| 4,271,192 | 6/1981 | Wurtman et al. | 514/567 |
| 4,327,112 | 4/1982 | Wurtman | 514/567 |
| 4,377,595 | 3/1983 | Wurtman | 514/567 |
| 4,426,378 | 1/1984 | Holaday | 514/18 |
| 4,542,123 | 9/1985 | Wurtman | 514/567 |

OTHER PUBLICATIONS

Zlokovic et al., "Slow Penetration of Thyrotropin-Releasing Hormone Across the Blood-Brain Barrier of an In Situ Perfused Guinea Pig Brain", *J. of Neurochem.*, 51(1): 252–257 (1988).

Togari et al., "Centrally mediated activation of tyrosine hydroxylation in rat adrenals by thyrotropin-releasing hormone", *Biochem. Pharmacol.*, 37(8): 1637–1639 (1988).

Cornford et al., "Blood-Brain Barrier Restriction of Peptides and the Low Uptake of Enkephalins", *Endocrinol.*, 103(4): 1297–1303 (1978).

Marek et al., "Thyrotropin-releasing hormone-increased catabolism of catecholamines in brains of thyroidectomized rats", *Biochem. Pharmocol.*, 26: 1817–1818 (1977).

Chase et al., "Hypothalamic Releasing Factors and Parkinson Disease", *Arch. Neurol.*, 31: 55–56 (1974).

McCaul et al., "Intravenous Thyrotrophin-Releasing Hormone in Parkinson's Disease", *The Lancet*, Apr. 20, 1974, p. 735.

Wurtman et al., "Brain Catechol Synthesis: Control by Brain Tyrosine concentration", *Science*, 185: 183–184 (1974).

Togari et al., Chemical Abstracts vol. 109, 1988, Abstract 32365h.

*Primary Examiner*—Mukund J. Shah
*Assistant Examiner*—Edward C. Ward
*Attorney, Agent, or Firm*—Hamilton, Brook, Smith & Reynolds

[57] ABSTRACT

Compositions useful in the treatment of inadequate neuronal dopamine release, as well as methods of use therefor. The compositions include drugs, such as thyrotropin-releasing hormone, which result in enhanced release of dopamine and tyrosine or a tyrosine precursor.

7 Claims, 1 Drawing Sheet

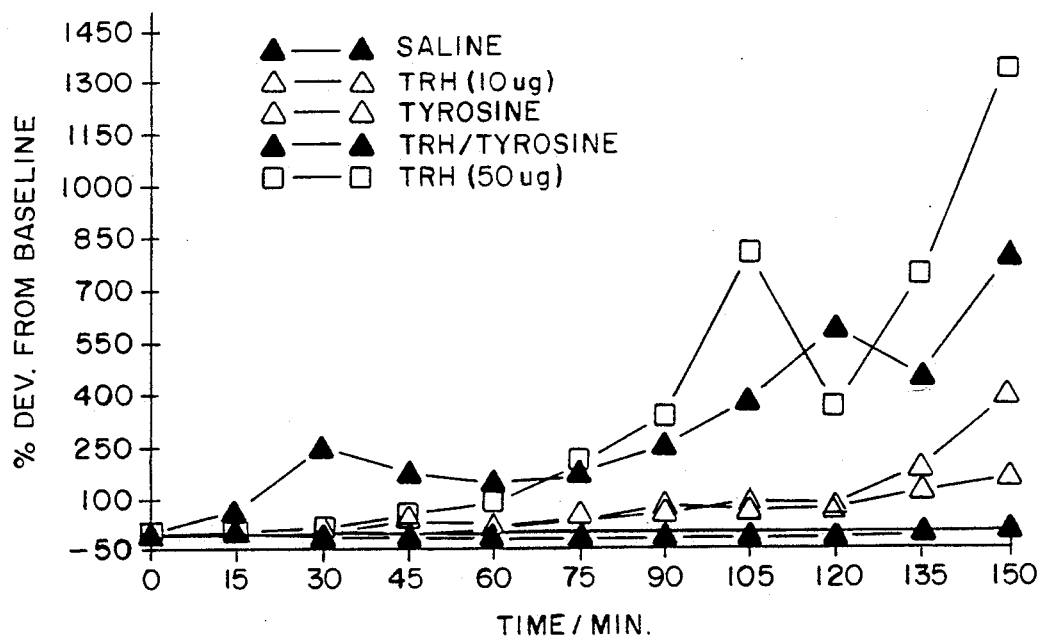

PROCESS AND COMPOSITION FOR INCREASING BRAIN DOPAMINE RELEASE

GOVERNMENT SUPPORT

Work described herein was supported by the Center for Brain Sciences and Metabolism Charitable Trust.

BACKGROUND

Parkinson's disease is a neurological disorder characterized by a deficiency of dopamine (3,4-dihydroxyphenylethylamine), particularly in the basal ganglia. The clinical features of Parkinsonism include tremor, bradykinesia, rigidity and disturbance of posture. Presently, Parkinson's disease is most commonly treated by administering a drug such as levodopa (L-Dopa) which improves skeletal muscle function by being decarboxylated to dopamine and acting on the central nervous system (CNS).

L-Dopa (L-3,4-dihydroxyphenylalanine), the metabolic precursor of dopamine, is a commonly administered dopaminergic drug. L-Dopa is also formed in the body from L-tyrosine. L-Dopa has the ability to permeate striatal tissue, where it is converted to dopamine. However, orally administered dopamine cannot cross the blood-brain barrier. Because L-dopa is decarboxylated in the peripheral circulation, large doses are generally needed to result in accumulation of dopamine in the brain unless the L-dopa is administered in conjunction with a second drug, such as carbidopa, to block decarboxylation outside the brain. The majority of patients with Parkinson's disease who are treated with L-dopa ultimately develop side effects such as dyskinesias and psychiatric disturbances. Some patients do not respond to L-Dopa. As a result, there is a concerted effort to develop substitute therapies for dopamine-dependent CNS disorders, such as Parkinsonism.

Thyrotropin-releasing hormone (TRH) is a tripeptide (L-pyroglutamyl-L-histidyl-L-prolineamide) which occurs in the hypothalamus and influences the release of thyroid-stimulating hormone and prolactin from the pituitary gland. Due to its action on the pituitary gland, TRH has been reported to affect behavior in man and has been proposed for the treatment of depression. There have also been reports of TRH-induced increase in norepinephrine metabolism in the brain, which is due to TRH activation of tyrosine hydroxylase (TH), the enzyme of the rate-limiting step in the conversion of tyrosine to L-dopa in catecholamine synthesis. Some studies of intraperitoneal administration of TRH in mice demonstrate a marked increase of L-dopa accumulation in the brain and adrenals, indicating activation of in vivo tyrosine hydroxylase by TRH. However, it is not generally believed that TRH has this affect, because it has not been thought that TRH readily crosses the blood-brain barrier.

The amino acid tyrosine is the precursor of catecholamine biosynthesis in all nerve cells which produce catecholamines. Tyrosine is converted to L-dopa by the rate-limiting enzyme tyrosine hydroxylase. Tyrosine has been shown to increase or decrease blood pressure depending on the original levels, reduce depression and treat and prevent ventricular fibrillation.

Wurtman et al. reported (*Science* 185: 183-184, Jul. 12, 1974) increases in brain tyrosine concentrations results in increases in brain DOPA concentrations It had previously been thought that changes in brain tyrosine levels would not affect tyrosine's conversion to L-dopa because of the rate-limiting enzyme tyrosine-hydroxylase. A method of treating Parkinsonism and other related CNS disorders which alleviates the effects of the condition and does not have the limitations of presently available methods would be very valuable.

SUMMARY OF THE INVENTION

The present invention is based on the discovery that administration to an individual of a drug which results in enhanced release of dopamine, either alone or in combination with tyrosine or a tyrosine precursor, results in an unexpected increase in neuronal dopamine release. Administration of such a drug, alone or in combination with tyrosine or a tyrosine precursor, is particularly valuable in treating an individual suffering from a central nervous system (CNS) disorder, such as Parkinson's Disease.

For example, thyrotropin-releasing hormone (TRH) or an analogue or metabolite thereof, can be administered, alone or in combination with tyrosine or a tyrosine precursor, to an individual to alleviate the symptoms of a CNS disorder, such as Parkinson's Disease. In the method of the present invention, TRH, a TRH analogue, a TRH metabolite, or a combination thereof, or a composition comprising 1) TRH, a TRH analogue, a TRH metabolite or a combination thereof, and 2) tyrosine and/or a tyrosine precursor can be administered in sufficient quantities to alleviate the symptoms.

BRIEF DESCRIPTION OF THE DRAWING

The FIGURE is a schematic representation of the effect of TRH and tyrosine on striatal dopamine release in rats. The x-axis corresponds to the time elapsed after the administration of TRH, tyrosine or TRH and tyrosine. The y-axis corresponds to the percent deviation from the baseline level of dopamine release due to the administration of TRH, tyrosine or TRH and tyrosine.

DETAILED DESCRIPTION OF THE INVENTION

The present invention relates to both methods and compositions useful in increasing striatal dopamine release and to their use in treating CNS disorders, such as Parkinson's Disease. In one embodiment of the method of the present invention, TRH, a TRH analogue, a TRH metabolite or a combination thereof is administered. In a second embodiment, compositions of the present invention are administered. Such compositions are administered to individuals for increasing neuronal dopamine release and comprise at least one drug which results in enhanced release of dopamine and tyrosine or a tyrosine precursor (e.g., phenylalanine). As used herein, the term drug is defined as any chemical agent that affects living processes. Goodman and Gilman's *The Pharmacological Basis of Therapeutics*, 6th edition, page 1.

Thyrotropin-releasing hormone (TRH), TRH analogues and TRH metabolites are of particular use for increasing neuronal dopamine release. As used herein, the term TRH refers to TRH, TRH analogues and TRH metabolites. In the method of the present invention, TRH alone, one or more TRH analogues or one or more TRH metabolites, alone or in combination, can be administered to alleviate the symptoms of dopamine-dependent CNS disorder. There are numerous TRH analogues, such as: pyro 2 aminoadipyl leucine prolinamide; pyro 2 aminoadipyl norvaline prolinamide; pyroglutamyl leucine pipecolamide; pyroglutamyl leucine thiazolidine 4-carboxylic acid amide; pyroglutamyl norvaline thiazolidine 4-carboxylic acid amide; gamma butyrolactone gamma carbonyl histidine-prolinamide; ortho histidine-prolinamide 5 fluoroimidazole TRH; pyro 2 aminoadipyl histidylthiazolidine 4-carboxylic acid amide; pyroglutamyl-3-methyl histidyl prolinamide. TRH metabolites include deamido TRH, prolinamide, histidylprolinamide, histitidylproline, and their diketopiperizine products. Tyrosine precursors include phenylalanine, and tyrosine-containing peptides, TRH, a TRH analogue or a TRH metabolite, or a combination thereof, can be administered alone or with tyrosine, a tyrosine precursor or a combination of both in amounts effective to increase striatal dopamine release and alleviate symptoms of the condition being treated.

The quantity of each drug to be administered will be determined on an individual basis and will be based at least in part on consideration of the individual's size. In general, the TRH dosage for an individual will range from 1.5 ug TRH per kg body weight to 30 ug TRH per kg body weight and the tyrosine dosage will range from 10 mg tyrosine per kg body weight to 500 mg tyrosine per kg body weight.

According to the method of the present invention, in which both TRH and tyrosine are administered, the drugs can be administered simultaneously or sequentially but must be given sufficiently close in time (e.g., generally within a 24 hour period of each other), to have the desired effect.

TRH alone or the composition of the present invention can be administered to an individual orally, by subcutaneous or other injection, parenterally (e.g., intracisternally intraperitoneally), rectally, transdermally or nasally. The form in which the composition will be administered (e.g., tablet, capsule, powder, solution) will depend on the route by which it is administered. In most cases, administration will generally be on a daily basis, but can be administered intermittently according to the patient's needs.

The composition of the present invention can optionally include, in addition to TRH and tyrosine, other components. The components included in a particular composition are determined primarily by the manner in which the composition is administered. For example, a composition to be administered orally in tablet form can include, in addition to TRH and tyrosine, a filler (e.g., lactose), a binder (e.g., carboxymethylcellulose, gelatin), a flavoring agent, an adjuvant, a coloring agent, and a coating material (e.g., wax or plasticizer).

The present invention will now be illustrated by the following Exemplification, which is not to be taken as limiting in any way.

Exemplification Assessment of the Effect of TRH and Tyrosine on Striatal Dopamine Release Groups of 7 male albino rats were implanted with a jugular venous catheter (for administering the drugs and withdrawing blood samples), and a microdialysis probe into the corpus striatum (for sampling fluid in equilibrium with intrasynaptic fluids).

Animals were placed under deep urethane anesthesia for the duration of the experiment. Each animal received 10 micrograms of TRH or a saline placebo, and/or tyrosine at a dose of 20 micrograms per kilogram, or a saline placebo.

Drugs were administered to the animals after it has been demonstrated that dopamine release (as assessed using the in vivo microdialysis) had been stable for 45 minutes. Microdialysis samples (23 microliters of artificial cerebrospinal fluid per sample) were then collected at 15 minute intervals for 150 minutes, and rapidly assayed for dopamine, its chief metabolites (DOPAC and HVA), serotonin, and the serotonin metabolite, 5-HIAA.

As shown in the FIGURE, administration of TRH (10 micrograms) alone caused a 190% increase (from the baseline) in dopamine release after two hours. Other compounds measured were stable. Administration of tyrosine alone caused an increase in dopamine release of about 110% after two hours.

More importantly, administering both tyrosine and TRH together resulted in an increased peak dopamine release of 450%. A higher dose of TRH (50 micrograms) without tyrosine had a greater effect than the lower dose (10 micrograms) of TRH of 750%.

Equivalents

Those skilled in the art will recognize, or be able to ascertain using no more than routine experimentation, many equivalents to the specific embodiment of the invention described specifically herein. Such equivalents are intended to be encompassed in the scope of the following claims.

What is claimed is:

1. A composition for administration to an individual for increasing neuronal dopamine release in the brain of the individual, consisting essentially of:
   a) TRH, a TRH analogue or a TRH metabolite, in sufficient amount to provide 1.5 to 30 $\mu$g of TRH per kg body weight; and
   b) tyrosine or a tyrosine precursor in sufficient amount to provide 10 to 500 mg of tyrosine per kg body weight.

2. A method of enhancing neuronal dopamine release in the brain of an individual, comprising administering to the individual an effective quantity of TRH, a TRH analogue, or a TRH metabolite, each alone or in combination.

3. A method of enhancing neuronal dopamine release in an individual, comprising administering to the individual an effective quantity of a composition consisting essentially of:
   a) TRH, a TRH analogue or a TRH metabolite in sufficient amount to provide 1.5 to 30 $\mu$g of TRH per kg body weight; and
   b) tyrosine in sufficient amount to provide 10 to 500 mg of tyrosine per kg body weight.

4. A method of treating inadequate striatal dopamine release in an individual, comprising administering to the individual an effective quantity of a composition consisting essentially of:
   a) TRH, a TRH analogue, or a TRH metabolite, in sufficient amount to provide 1.5 to 30 $\mu$g of TRH per kg body weight; and
   b) tyrosine or a tyrosine precursor, in sufficient amount to provide 10 to 500 mg of tyrosine per kg body weight.

5. A method of treating Parkinson's Disease in an individual, comprising administering to the individual an effective quantity of TRH, a TRH analogue, a TRH metabolite, alone or in combination, in sufficient amount to provide 1.5 to 30 $\mu$g of TRH per kg body weight.

6. A method of claim 5 wherein the TRH metabolite is selected from the group consisting of: deamido TRH, prolinamide, histidylprolinamide and histidylproline, and their diketopiperizine products.

7. A method of treating Parkinson's Disease in an individual, comprising administering to the individual an effective quantity of a composition consisting essentially of:
 a) TRH, a TRH analogue or a TRH metabolite, in sufficient amount to provide 1.5 to 30 µg of TRH per kg body weight; and
 b) tyrosine in sufficient amount to provide 10 to 500 mg of tyrosine per kg body weight.

* * * * *